(12) United States Patent
Jansen

(10) Patent No.: US 11,027,065 B2
(45) Date of Patent: *Jun. 8, 2021

(54) MEDICAL ADMINISTRATION BARREL WITH GROOVES AND METHOD OF SEALING SAME

(71) Applicant: West Pharmaceutical Services, Inc., Exton, PA (US)

(72) Inventor: Hubert Jansen, Stolberg (DE)

(73) Assignee: WEST PHARMACEUTICAL SERVICES, INC., Exton, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/778,690

(22) Filed: Jan. 31, 2020

(65) Prior Publication Data

US 2020/0164144 A1 May 28, 2020

Related U.S. Application Data

(63) Continuation of application No. 15/758,890, filed as application No. PCT/US2015/049588 on Sep. 11, 2015, now Pat. No. 10,603,434.

(51) Int. Cl.
*A61M 5/28* (2006.01)
*A61M 5/178* (2006.01)
(Continued)

(52) U.S. Cl.
CPC ............ *A61M 5/1782* (2013.01); *A61M 5/28* (2013.01); *A61M 5/3129* (2013.01);
(Continued)

(58) Field of Classification Search
CPC ...... A61M 5/1782; A61M 5/28; A61M 5/281; A61M 5/2053; A61M 5/3129;
(Continued)

(56) References Cited

U.S. PATENT DOCUMENTS

| 5,779,668 | A | ‡ | 7/1998 | Grabenkort | A61M 5/3129 604/191 |
| 5,788,670 | A | * | 8/1998 | Reinhard | A61M 5/3129 604/191 |
| 8,632,493 | B2 | ‡ | 1/2014 | Cali et al. | A61M 5/3234 604/110 |
| 2013/0303995 | A1 | ‡ | 11/2013 | Tachikawa | A61M 5/28 604/240 |

(Continued)

FOREIGN PATENT DOCUMENTS

| JP | H02280764 A | ‡ | 11/1990 |
| JP | H02280764 A | | 11/1990 |

(Continued)

OTHER PUBLICATIONS

Int'l Search Report & Written Opinion dated Jun. 7, 2016 in Int'l Application No. PCT/US2015/049588.‡

(Continued)

*Primary Examiner* — Matthew W Jellett
(74) *Attorney, Agent, or Firm* — Panitch Schwarze Belisario & Nadel LLP

(57) ABSTRACT

A barrel is provided having open proximal end and a closed distal end, and at least one groove in an interior wall thereof. The groove(s) define a length extending a distance from the open end of the barrel toward the distal end of the barrel and defining a substantially constant depth and width along the length thereof. A piston is in sealing engagement with the interior wall of the barrel. The groove(s) permits fluid to bypass the piston when positioned along the groove(s). At least a portion of the piston is positioned distally from the groove(s), thereby sealing substance within the barrel.

9 Claims, 2 Drawing Sheets

FIG. 2

(51) Int. Cl.
  *B65B 3/00* (2006.01)
  *B65B 7/28* (2006.01)
  *A61M 5/31* (2006.01)
  *A61M 5/315* (2006.01)

(52) U.S. Cl.
  CPC .......... *A61M 5/3135* (2013.01); *B65B 3/006* (2013.01); *B65B 7/2821* (2013.01); *A61M 5/31511* (2013.01); *A61M 2005/3123* (2013.01)

(58) Field of Classification Search
  CPC ............. A61M 5/3135; A61M 5/31511; B65B 3/006; B65B 7/2821
  See application file for complete search history.

(56) References Cited

U.S. PATENT DOCUMENTS

| | | | |
|---|---|---|---|
| 2015/0190578 A1 ‡ | 7/2015 | Okihara et al. ....... | B65B 31/027 53/432 |
| 2017/0072130 A1 ‡ | 3/2017 | McMahon ............ | A61M 5/002 |

FOREIGN PATENT DOCUMENTS

| | | | | |
|---|---|---|---|---|
| JP | H07313598 A | ‡ | 12/1995 | |
| JP | H07313598 A | | 12/1995 | |
| JP | H09299480 A | ‡ | 11/1997 | |
| JP | H09299480 A | | 11/1997 | |
| JP | H11504536 A | ‡ | 4/1999 | |
| JP | H11504536 A | | 4/1999 | |
| JP | 2002219170 A | ‡ | 8/2002 | .............. A61M 5/28 |
| JP | 2002219170 A | | 8/2002 | |
| WO | 9630066 A1 | | 10/1996 | |
| WO | WO-9630066 A1 | ‡ | 10/1996 | ........ A61M 5/31596 |
| WO | 9819715 A1 | | 5/1998 | |
| WO | WO-9819715 A1 | ‡ | 5/1998 | .............. A61L 2/07 |
| WO | 2014181474 A1 | | 11/2014 | |
| WO | WO-2014181474 A1 | ‡ | 11/2014 | ........... B65B 7/2821 |

OTHER PUBLICATIONS

Int'l Preliminary Report on Patentability dated Mar. 22, 2018 in Int'l Application No. PCT/US2015/049588.‡

\* cited by examiner
‡ imported from a related application

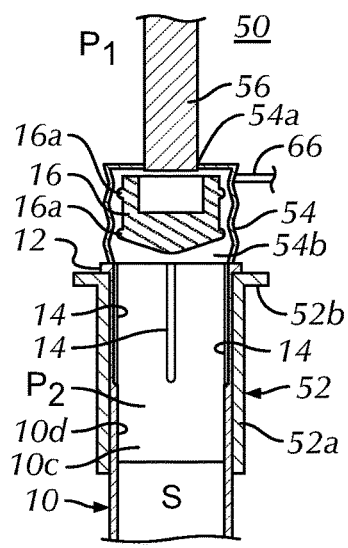
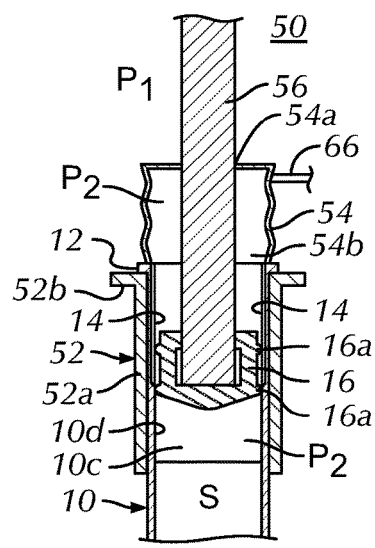
FIG. 3A     FIG. 3B
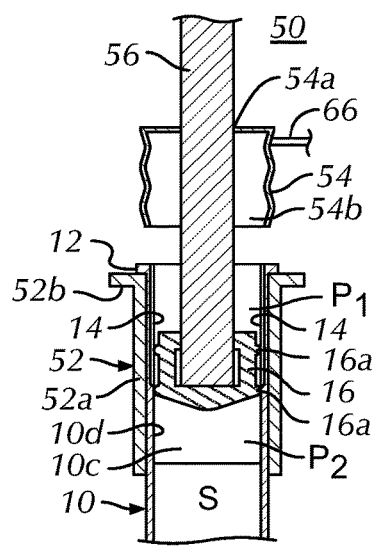
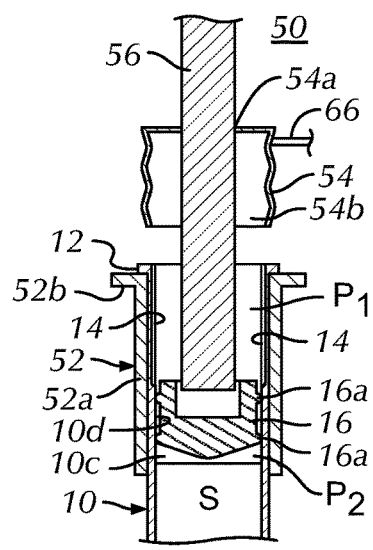
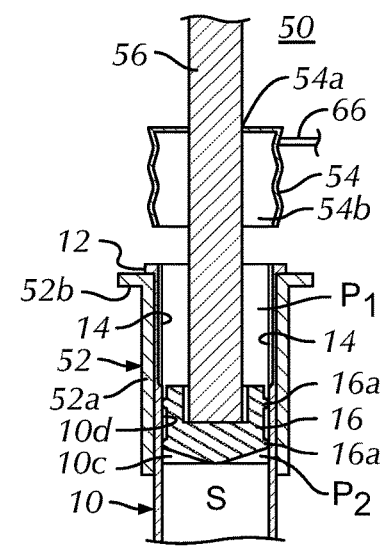
FIG. 3C     FIG. 3D     FIG. 3E

MEDICAL ADMINISTRATION BARREL WITH GROOVES AND METHOD OF SEALING SAME

CROSS-REFERENCE TO RELATED APPLICATION

This application claims the benefit of co-pending U.S. patent application Ser. No. 15/758,890, titled "Medical Administration Barrel with Grooves and Method of Sealing Same", filed on Mar. 9, 2018, which is a section 371 of International Application No. PCT/US15/49588, filed Sep. 11, 2015, which was published in the English language on Mar. 16, 2017 under International Publication No. WO 2017/044112 A1, the disclosure of which is incorporated herein by reference.

BACKGROUND OF THE INVENTION

The present invention generally relates to a medical administration barrel and a method of sealing the barrel, and, particularly, to a medical administration barrel having grooves assisting in minimizing headspace between a piston and substance within the barrel during the sealing process.

Vacuum piston placement is a piston placement process utilized to insert a piston into an open end of a pre-filled container in order to seal off the substance within the container in an airtight manner from the exterior environment. Generally, the piston and the pre-filled container are exposed to a vacuum, i.e., a pressure lower than atmospheric pressure, and then the piston is thereafter sealingly engaged with the open end of the container. The exterior of the piston and container assembly is thereafter restored to atmospheric pressure, such that a pressure differential is created across the piston between the proximal and distal surfaces thereof. The pressure differential drives the piston down the barrel until the friction force balances the pressure difference. Afterwards, the piston may be further advanced, e.g., by a pushing member, until pressure equilibrium is reached across the piston.

One drawback of the vacuum piston placement process is that where a low volume of substance is filled in a larger container, a large amount of headspace, i.e., the space between the distal surface of the piston and the substance, may still remain after the piston reaches the position associated with pressure equilibrium. For example, the headspace volume may equal approximately 30% of the volume of the substance filled within the container.

One approach to minimizing headspace between the piston and the substance filled inside the container may be to utilize smaller containers. For example, a container may be sized to fit only the piston height, in addition to the length associated with the desired volume of the filled substance. However, where an administration system located behind the piston is utilized to drive the piston forward during use of the container (e.g., when injecting the substance within the container into a recipient), the smaller sized container may not have the necessary space to accommodate the administration system behind the piston. Accordingly, where an administration system is present, the longer container is necessary.

Nonetheless, the sealed container may be exposed to different chemical and/or environmental changes during transport that may potentially cause retraction and ejection of the piston out of the open end of the container. For example, the container may be exposed to sub-atmospheric pressure during air transportation, or travel through high elevation regions, which may lead to retraction of the piston. As another example, the container may be exposed to extreme temperatures, which may lead to retraction of the piston. As yet another example, an internal reaction of the substance within the container may cause a change in headspace gas pressure, which may also lead to retraction of the piston. Further, the relatively large air bubble constituting the headspace and trapped within the container may be problematic when dispensing the substance thereafter.

Therefore, it is desirable to manufacture a container configured to receive the piston and, if employed, an administration system behind the piston, and also assist in further advancing the piston into the container when utilizing the vacuum piston placement process, to minimize headspace volume.

BRIEF SUMMARY OF THE INVENTION

Briefly stated, one aspect of the present invention is directed to a method of minimizing headspace between a substance filled in a medical administration barrel and a piston sealing off an open proximal end of the medical administration barrel. The medical administration barrel has at least one groove in an interior wall thereof, the at least one groove defining a length extending a distance from the open end of the medical administration barrel toward an opposing distal end of the medical administration barrel. The at least one groove permits fluid to bypass the piston when positioned along the at least one groove.

The method comprises the steps of sealingly engaging a vacuum enclosure with the proximal open end of the medical administration barrel, the vacuum enclosure receiving the piston therein; applying a vacuum to an interior of the sealed vacuum enclosure and medical administration barrel, such that pressure within the sealed vacuum enclosure and medical administration barrel is less than pressure external to the medical administration barrel; physically advancing the piston into the medical administration barrel along the length of the at least one groove, the at least one groove permitting fluid to bypass the piston. Thereafter, the method further comprises the step of ceasing physical advancement of the piston upon reaching an initial portion of the interior wall of the medical administration barrel free of the at least one groove, thereby sealingly engaging the interior wall of the medical administration barrel and providing an air-tight seal inside a portion of the medical administration barrel between the piston and a distal end of the medical administration barrel and maintaining the vacuum between the piston and the substance positioned within the medical administration barrel. Lastly, the method comprises the step of disengaging the vacuum enclosure from the proximal open end of the medical administration barrel, thereby relieving a portion of the medical administration barrel between the piston and the proximal open end of the medical administration barrel from the vacuum and creating a pressure differential across the piston causing the piston to slide further toward the substance in the medical administration barrel and minimizing the headspace between the substance and the piston.

Another aspect of the present invention is directed to a sealed medical administration barrel. The sealed medical administration barrel comprises a medical administration barrel having an open proximal end and a closed distal end, and at least one groove in an interior wall thereof. The at least one groove defines a length extending a distance from the open end of the medical administration barrel toward the distal end of the medical administration barrel and defining a substantially constant depth and width along the length thereof. A substance is contained within the medical administration barrel, having a predetermined volume; and a piston is sealing engagement with the interior wall of the medical administration barrel. The at least one groove permits fluid to bypass the piston when positioned along the at least one groove. At least a portion of the piston is positioned distally from the at least one groove, thereby sealing the substance within the medical administration barrel.

BRIEF DESCRIPTION OF THE DRAWINGS

The foregoing summary, as well as the following detailed description of a preferred embodiment of the present invention, will be better understood when read in conjunction with the appended drawings. For the purpose of illustrating the disclosure, there is shown in the drawings a preferred embodiment of a medical administration barrel. It should be understood, however, that the disclosure is not limited to the precise arrangements and instrumentalities shown. In the drawings:

FIG. 3A is a partial cross-sectional, elevational view of the medical administration barrel of FIG. 1 mounted in the vacuum piston placement device of FIG. 2, with the vacuum enclosure sealingly engaging the open end of the barrel and the piston positioned in the vacuum enclosure;

FIG. 3B is a partial cross-sectional, elevational view of the medical administration barrel of FIG. 1 mounted in the vacuum piston placement device of FIG. 2, with the pushing member physically advancing the piston into the barrel;

FIG. 3C is a partial cross-sectional, elevational view of the medical administration barrel of FIG. 1 mounted in the vacuum piston placement device of FIG. 2, with the piston physically advanced into the barrel by the pushing member and the vacuum enclosure disengaged from the barrel;

FIG. 3D is a partial cross-sectional, elevational view of the medical administration barrel of FIG. 1 mounted in the vacuum piston placement device of FIG. 2, with the piston further advanced into the barrel under the drive of a pressure differential across the piston; and FIG. 3E is a partial cross-sectional, elevational view of the medical administration barrel of FIG. 1 mounted in the vacuum piston placement device of FIG. 2, with the pushing member further physically advancing the piston into the barrel to substantially achieve pressure equilibrium across the piston.

DESCRIPTION OF THE DISCLOSURE

Figure 2:
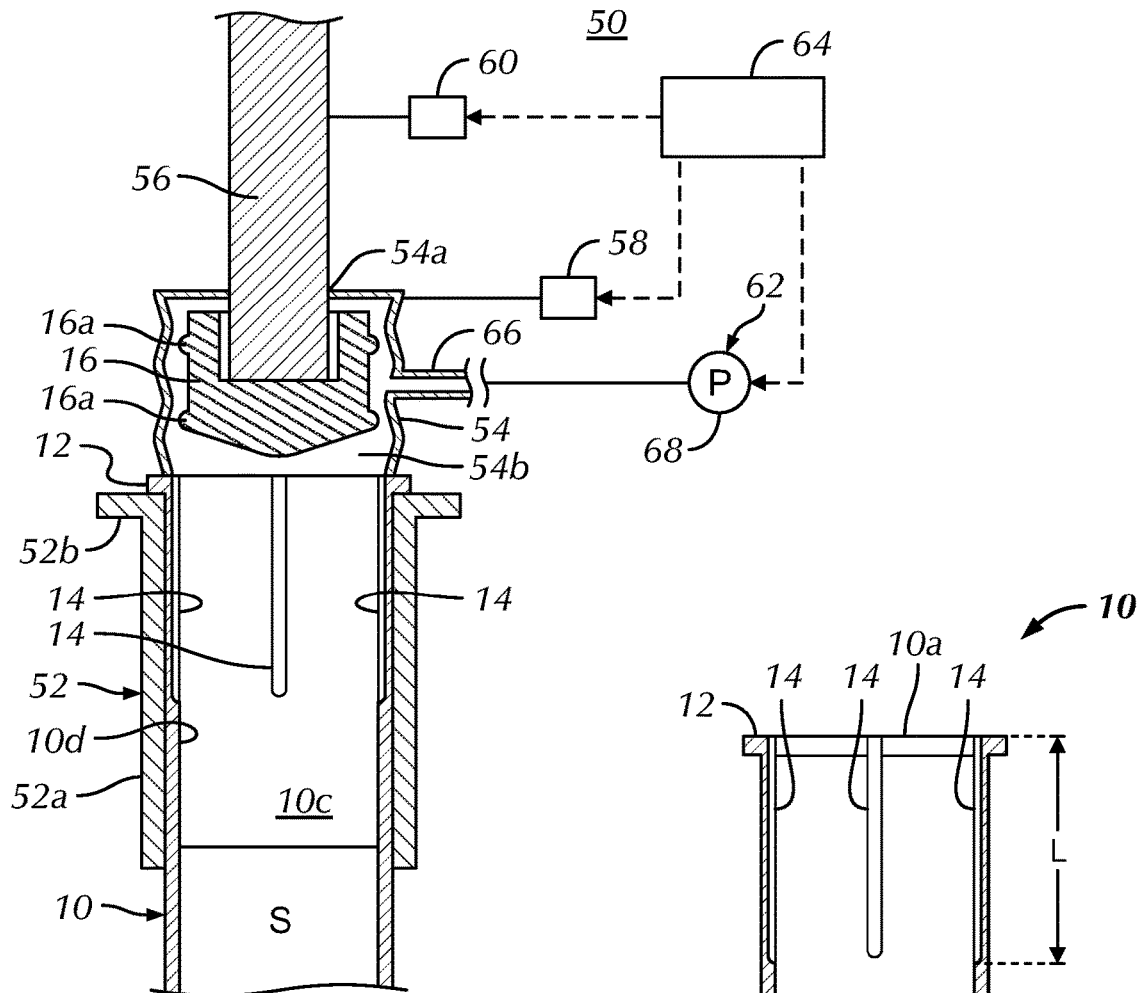
FIG. 2 is a schematic diagram of a vacuum piston placement device utilized for placing a piston in a pre-filled medical administration barrel of FIG. 1 and sealing an open end thereof.

Certain terminology is used in the following description for convenience only and is not limiting. The words "lower," "bottom," "upper" and "top" designate directions in the drawings to which reference is made. The words "inwardly," "outwardly," "upwardly" and "downwardly" refer to directions toward and away from, respectively, the geometric center of the medical administration barrel, and designated parts thereof, in accordance with the present disclosure. Unless specifically set forth herein, the terms "a," "an" and "the" are not limited to one element, but instead should be read as meaning "at least one." The terminology includes the words noted above, derivatives thereof and words of similar import.

It should also be understood that the terms "about," "approximately," "generally," "substantially" and like terms, used herein when referring to a dimension or characteristic of a component of the invention, indicate that the described dimension/characteristic is not a strict boundary or parameter and does not exclude minor variations therefrom that are functionally the same or similar. At a minimum, such references that include a numerical parameter would include variations that, using mathematical and industrial principles accepted in the art (e.g., rounding, measurement or other systematic errors, manufacturing tolerances, etc.), would not vary the least significant digit.

Figure 1:
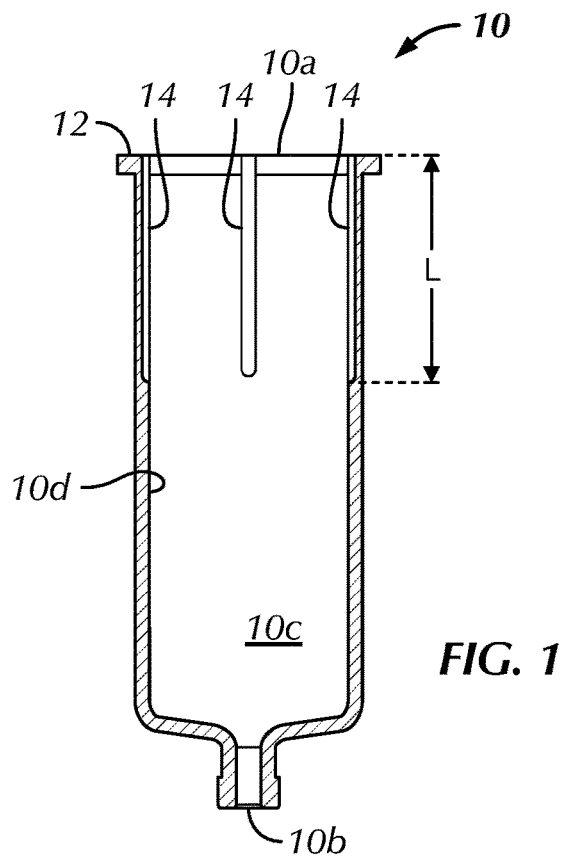
FIG. 1 is a cross-sectional, elevational view of an unsealed medical administration barrel, according to a preferred embodiment of the invention.

Referring to the drawings in detail, wherein the same reference numerals indicate like elements throughout, there is shown in FIG. 1 a medical administration barrel, generally designated 10, in accordance with a preferred embodiment of the present invention. As should be understood by those of ordinary skill in the art, the medical administration barrel 10 may take the form of any container having a cavity or a chamber capable of being filled with a substance, such as, for example, without limitation, a syringe, a cartridge, or the like.

The barrel 10 includes an open proximal end 10a, an opposing a closed distal end 10b, and a chamber 10c therebetween. The chamber 10c defines an interior wall 10d extending between the proximal and distal ends 10a, 10b. As should be understood by those of ordinary skill in the art, the closed distal end 10b may take the form of any sealed end through which fluid communication from outside of the barrel 10 may be established with the chamber 10c, such as, for example, without limitation, a pierceable septum, a tip having a removable sealing cap, or the like. In the illustrated embodiment, the barrel 10 further includes a flange 12 laterally extending from the open proximal end 10a. However, the barrel 10 may alternatively not include a flange 12, or include a differently configured flange 12.

The barrel 10 further includes at least one groove 14 in the interior wall 10d thereof, longitudinally extending a length L from the proximal open end 10a toward the distal end 10b. In the illustrated embodiment, the barrel 10 includes a plurality of grooves 14 defining substantially the same length L. Each of the grooves 14 also defines a substantially constant depth and width along the length L thereof.

In one embodiment, for example, the medical administration barrel 10 is a 10 ml cartridge. The 10 ml cartridge includes a plurality of grooves 14 defining a length L between approximately 5 mm and approximately 25 mm. Preferably, the grooves 14 define a length L of approximately 20 mm. The plurality of grooves 14 also define a substantially constant depth along the length L, between approximately 0.2 mm and approximately 0.6 mm, and a substantially constant width along the length L, between approximately 1 mm and 4 mm.

After a predetermined volume of substance S (FIGS. 3A-3E) is filled into the chamber 10c, e.g., between approximately 3 ml to approximately 10.5 ml, a piston 16 (FIGS. 2, 3A-3E) is advanced into the chamber 10c, via the open proximal end 10a of the barrel 10. The piston 16 is configured to sealingly engage the interior wall 10d of the barrel 10, thereby providing an air-tight seal for the substance S within the chamber 10c from the external environment. In one embodiment, the piston 16 includes at least one annular rib 16a projecting radially therefrom for slidable sealing engagement with the interior wall 10d of the medical administration barrel 10. In the illustrated embodiment, the piston 16 includes two axially-spaced annular ribs 16a. However, as should be understood by those of ordinary skill in the art, the piston 16 may include more than two ribs 16a, or, alternatively, may be constructed with no ribs 16a, but rather be dimensioned such that the radial periphery thereof entirely or predominantly sealingly engages the interior wall 10d and provide and air-tight seal therebetween.

The at least one groove 14, dimensioned as described above, permits fluid, e.g., gas, to bypass the piston 16 when the piston 16 is positioned inside the barrel 10 along the at least one groove 14. The piston 16, therefore, seals the chamber 10c (and the substance S therein) once at least a portion of the piston 16 is positioned inside the barrel 10 distally from the at least one groove 14. For example, in the illustrated embodiment, gas may bypass the piston 16 through the grooves 14, when both annular ribs 16a of the piston 16 are positioned along the grooves 14. Once at least the distal most annular rib 16a is advanced past the grooves 14, the piston 16 seals the chamber 10c.

The piston 16 may be placed into the medical administration barrel 10 via the vacuum piston placement method, understood by those of ordinary skill in the art. FIG. 2 is a schematic view of a vacuum piston placement device ("PPD") 50. As shown, the PPD 50 includes a barrel supporting member 52, a vacuum enclosure 54, a pushing member 56, a vacuum enclosure moving mechanism 58, an actuator 60, a pressure control mechanism 62, and a control unit 64.

As shown, the medical administration barrel 10, pre-filled with the predetermined volume of substance S, is supported by the barrel supporting member 52 of the PPD 50. In the illustrated embodiment, the barrel 10 is received within a complementary tube 52a of the supporting member 52 and the flange 12 of the barrel 10 is axially supported by a laterally extending flange 52b of the supporting member 52. As should be understood by those of ordinary skill in the art, however, the barrel 10 may be axially supported in the PPD 50 via any of numerous methods, currently know or that later become known.

The vacuum enclosure 54 is movable to sealingly engage and cover the proximal open end 10a of the barrel 10 in an airtight manner. The vacuum enclosure moving mechanism 58 moves the vacuum enclosure 54 under the control of the control unit 64. As should be understood by those of ordinary skill in the art, examples of the vacuum enclosure moving mechanism 58 include, but are not limited to, a fluid pressure cylinder device, a motor and the like.

The pushing member 56 is disposed to be movable along generally a center axis of the vacuum enclosure 54. In the illustrated embodiment, the pushing member 56 has a rod-like shape, but may alternatively take the form of other shapes. The pushing member 56 extends through an insertion hole 54a, formed in a proximal end of the vacuum enclosure 54, and into an interior chamber 54b of the vacuum enclosure 54. The pushing member 56 is advance-able and retractable through the insertion hole 54a in a slidable, airtight manner. For example, the vacuum enclosure 54 may include a sealing member (not shown), in slidable contact with the outer periphery of the pushing member 56. The actuator 60 advances and retracts the pushing member 56 under the control of the control unit 64. As should be understood by those of ordinary skill in the art, examples of the actuator 60 include, but are not limited to, a fluid pressure cylinder device, a motor, and the like.

The pressure control mechanism 62 includes an air line 66 with one end connected in fluid communication with the vacuum enclosure 54 and the other end connected with a vacuum source 68, such as, for example, without limitation, a vacuum pump. Under the control of the control unit 64, the vacuum source 68 of the pressure control mechanism 62 is operated, whereby air in the chamber 54b of the vacuum enclosure 54 is withdrawn via the air line 66, thereby reducing pressure in the vacuum enclosure chamber 54b and the medical administration barrel chamber 10c to a desired reduced pressure, as explained further below.

The process of placing the piston 16 into the pre-filled medical administration barrel 10 via vacuum placement, utilizing the PPD 50, will next be described. As shown in FIG. 3A, the medical administration barrel 10, filled with a predetermined amount of the substance S, is held by the supporting member 52 with the distal end 10b of the barrel 10 being oriented at the bottom. The vacuum enclosure moving mechanism 58 then advances the vacuum enclosure 54 into sealing engagement with the flange 12 of the barrel 10. The piston 16 is initially positioned within the chamber 54b of the vacuum enclosure 54, just above the open proximal end 10a of the barrel 10. Alternatively, the piston 16 may be physically advanced into the barrel 10 and positioned along the extent of the grooves 14. With this, the chamber 10c of the barrel 10 and the chamber 54b of the vacuum enclosure 54 are in sealed fluid communication and form an airtight space, isolated from the external atmosphere outside the barrel 10 and the vacuum enclosure 54.

Thereafter, the vacuum source 68 is operated to apply a vacuum to the chambers 54b and 10c, thereby reducing the pressure therein to a predetermined pressure $P_2$. Thus, the pressure $P_2$ inside the chambers 54b and 10c is lower than atmospheric pressure $P_1$ (approximately 1 bar) outside of the vacuum enclosure 54 and the barrel 10. The piston 16, positioned within the chamber 54b, or partially within the barrel 10 along the extent of the grooves 14, is not exposed to a pressure differential, because the chambers 54b and 10c are in fluid communication.

As shown in FIG. 3B, after the pressure in the chambers 54b and 10c is reduced to the desired pressure $P_2$, the pushing member 56 is advanced by the actuator 60 to engage the piston 16 and physically advance the piston 16 into the barrel 10 through the open proximal end 10a thereof toward the substance S. As the piston 16 is physically advanced into the barrel 10, along the span of the grooves 14, fluid, e.g., air, within the barrel 10 forward (distal) of the piston 16 is displaceable to the rear of the piston 16 via the grooves 14, bypassing the piston 16 and the annular ribs 16a. Therefore, as the piston 16 is advanced into the barrel 10 along the span of the grooves 14, the pressure $P_2$ remains the substantially same within both of the chambers 54b and 10c.

The pushing member 56 physically advances the piston 16 into the barrel 10 until at least an initial portion of the piston 16 surpasses the grooves 16 and sealingly engages substantially the entire interior wall 10d of the groove along a cross-section thereof. In the illustrated embodiment, physical advancement of the piston 16 is ceased when the distal most annular rib 16a reaches an initial portion of the interior wall 10d of the barrel 10 past the length L of the grooves 14 (FIGS. 3B, 3C). Because the distal most annular rib 16a is positioned in sealing engagement with the entire interior wall 10d of the barrel 10 along a cross-section thereof, i.e., the annular rib 16a is located past the grooves 14 previously creating a space between the annular rib 16a and the interior wall 10d, the piston 16 provides an airtight seal inside the portion of the barrel 10 defined between the piston 16 and the distal end 10b of the barrel 10.

Thereafter, as shown in FIG. 3C, the vacuum enclosure 54 is disengaged from the proximal open end 10a of the barrel 10, i.e., the vacuum enclosure 54 is retracted, thereby releasing the vacuum applied to the vacuum enclosure 54 and the barrel 10. Accordingly, the portion of the medical administration barrel 10 between the piston 16 and the proximal open end 10a of the barrel 10 is no longer sealed and returns to atmospheric pressure $P_1$. The portion of the barrel 10 between the piston 16 and the distal end 10b of the barrel 10 remains sealed, and, therefore, the vacuum pressure $P_2$ is maintained. Consequently, a pressure differential is created across the piston 16, driving the piston 16 forward (without being pushed by the pushing member 56) further toward the substance S (FIG. 3D), as should be understood by those of ordinary skill in the art.

As also should be understood by those of ordinary skill in the art, because the piston 16 is sealingly engaged with the interior wall 10d of the barrel 10 during the movement thereof due to the pressure differential across the piston 16, the portion of the barrel 10 between the piston 16 and the distal end 10b of the barrel comprises a sealed chamber, and fluid, e.g., air, can no longer escape. Accordingly, as the piston 16 is advanced further toward the substance S, the volume of the headspace between the piston 16 and the substance S decreases, and, therefore, the pressure $P_2$ progressively increases. The piston 16, thus, advances further toward the substance S under the drive of the pressure differential across the piston 16 until the increasing pressure $P_2$, between the piston 16 and the substance S, is approximately equilibrated with the atmospheric pressure $P_1$ proximal of the piston 16. Such forward advancement due to the pressure differential across the piston 16 minimizes the headspace between the piston 16 and the substance S.

As the piston 16 is advanced further toward the substance S, and, therefore, pressure differential across the piston 16 approximately equilibrates, frictional forces between the annular ribs 16a of the piston 16 and interior wall 10d of the barrel 10 may stop the piston 16 before equilibrium between $P_2$ and $P_1$ is substantially reached. Accordingly, after the piston 16 ceases forward advancement under the effect of the pressure differential across the piston 16, the pushing member 56 is re-engaged with the piston 16 and physically further advances the piston 16 toward the substance S to substantially equilibrate the pressure in the barrel 10 between the piston 16 and the substance S, and atmospheric pressure (FIG. 3E), thereby further minimizing the headspace between the piston 16 and the substance S.

It will be appreciated by those skilled in the art that changes could be made to the embodiment described above without departing from the broad inventive concept thereof. It is understood, therefore, that this disclosure is not limited to the particular embodiments disclosed, but it is intended to cover modifications within the spirit and scope of the present disclosure as defined by the appended claims.

I claim:

1. A vacuum piston placement system comprising:
   a barrel filled with a volume of substance, the barrel having an open proximal end and at least one groove in an interior of the barrel, the at least one groove defining a length extending a distance from the open proximal end toward an opposing distal end of the barrel;
   a piston;
   a vacuum enclosure configured to receive the piston and being movable into sealed engagement with the proximal open end of the barrel;
   a vacuum source in fluid communication with the vacuum enclosure and configured to apply a vacuum to an interior of the sealed vacuum enclosure and barrel to achieve a lower pressure within the sealed vacuum enclosure and barrel than pressure external to the barrel;
   an actuator configured to advance the piston from the vacuum enclosure into the barrel along the length of the at least one groove, the at least one groove permitting fluid to bypass the piston, and the actuator being further configured to cease advancement of the piston upon reaching an initial portion of the interior wall of the barrel free of the at least one groove, thereby sealingly engaging the interior wall of the barrel and providing an air-tight seal inside a portion of the barrel between the piston and the distal end of the barrel and maintaining the vacuum between the piston and the volume of substance within the barrel;
   wherein the vacuum enclosure is further configured to disengage from the proximal open end of the barrel, thereby relieving a portion of the barrel between the piston and the proximal open end of the barrel from the vacuum and creating a pressure differential across the piston to cause the piston to slide further toward the substance in the barrel and minimize headspace between the volume of substance and the piston.

2. The system of claim 1, further comprising a barrel supporting member having a top surface, and wherein the barrel includes a laterally extending flange, the barrel being received within a complementary tube of the supporting member, and the flange of the barrel being axially supported by the top surface of the supporting member.

3. The system of claim 1, further comprising a pushing member movable along an axis of the vacuum enclosure, the pushing member configured to extend through an insertion hole formed in a proximal end of the vacuum enclosure and into an interior chamber of the vacuum enclosure, wherein the actuator is configured to drive the pushing member to engage and advance the piston into the barrel through the open proximal end thereof.

4. The system of claim 1, wherein the piston includes at least one annular rib projecting radially therefrom for slidable sealing engagement with the interior wall of the barrel, the at least one annular rib being configured to sealingly engage a portion of the interior wall of the barrel free of the at least one groove, thereby providing the air-tight seal inside the portion of the barrel between the piston and the distal end of the barrel.

5. The system of claim 4, wherein the piston includes two axially-spaced annular ribs.

6. The system of claim 1, wherein the length of the at least one groove is within the range of 5 mm to 25 mm.

7. The system of claim 1, wherein the length of the at least one groove is 20 mm.

8. The system of claim 1, wherein the at least one groove defines a depth within the range of 0.2 mm to 0.6 mm.

9. The system of claim 1, wherein the at least one groove defines a width within the range of 1 mm to 4 mm.

* * * * *